United States Patent [19]

Fukumoto et al.

[11] Patent Number: 4,918,252

[45] Date of Patent: Apr. 17, 1990

[54] 1-HALO-(Z,E)-7,10-DODECADIENE AND A METHOD FOR THE PREPARATION THEREOF

[75] Inventors: Takehiko Fukumoto; Akira Yamamoto, both of Niigata, Japan

[73] Assignee: Shin-Etsu Chemical Co., Ltd., Tokyo, Japan

[21] Appl. No.: 333,462

[22] Filed: Feb. 5, 1989

[30] Foreign Application Priority Data

Apr. 12, 1988 [JP] Japan ............................ 63-90129

[51] Int. Cl.$^4$ ............................................. C07C 21/19
[52] U.S. Cl. ..................................... 570/189; 570/216; 570/219
[58] Field of Search ........................ 570/189, 216, 219

[56] References Cited

U.S. PATENT DOCUMENTS 2,038,593  4/1936  Muskat ................................ 570/189
3,947,505  3/1976  Helmlinger et al. ................. 570/189

FOREIGN PATENT DOCUMENTS 0241335  10/1987  European Pat. Off. ............ 570/189

*Primary Examiner*—Werren B. Lone
*Attorney, Agent, or Firm*—Wyatt, Gerber, Burke and Badie

[57] ABSTRACT

A novel and efficient synthetic route is proposed for the preparation of (Z,E)-9,12-tetradecadienyl acetate as a sex pheromone compound used for population control of the pest insects belonging to the genus of *Spodoptera* via an intermediate 1-halo-(Z,E)-7,10-dodecadiene, which is a novel compound not known in the prior art. This novel compound is synthesized by reacting a Grignard reagent $XMgC{\equiv}C(CH_2)_6X$, X being Cl or Br, with (E)-2-butenyl chloride or bromide to form an ene-yne compound of the formula $CH_3CH{=}^{(E)}CHCH_2C{\equiv}C(CH_2)_6X$ and then partially hydrogenating this ene-yne compound.

3 Claims, No Drawings

1-HALO-(Z,E)-7,10-DODECADIENE AND A METHOD FOR THE PREPARATION THEREOF

BACKGROUND OF THE INVENTION

The present invention relates to a 1-halo-(Z,E)-7,10-dodecadiene which is a novel compound and a method for the preparation of this compound. The compound is a useful intermediate for the synthesis of (Z,E)-9,12-tetradecadienyl acetate which is a sex pheromone of the insects belonging to the genus of Spodoptera as a kind of noxious pests in agriculture.

(Z,E)-9,12-Tetradecadienyl acetate is known as a sex pheromone of the insects belonging to the genus of Spodoptera and used for population control of the noxious insectan pest in agriculture. Several methods are known for the synthetic preparation of this compound including a method utilizing the Wittig reaction described in Japanese Patent Kokai 50-53312 and 50-58005 and Tetrahedron Letters, volume 1974, page 779, a method utilizing an organo-lithium compound described in Science, volume 170, page 542 (1970) and so on. These prior art methods, however, are not quite satisfactory in industrial production of the compound because each of the methods involves a complicate process of synthesis and requires special and expensive starting materials.

Besides, a method utilizing a Grignard reaction is known for the synthesis of (Z,E)-9,12-tetradecadienyl acetate (see Bull. Soc. Chim. France, volume 1962, page 315 and volume 1963, page 1449). This method is also defective because of the low yield of the desired product and formation of a by-product by the allyl rearrangement reaction which can be separated from the reaction mixture only with great difficulties. Accordingly, it is eagerly desired to develop a novel and advantageous method for the industrial production of (Z,E)-9,12-tetradecadienyl acetate.

The extensive investigations undertaken with an object to solve the above mentioned problem have led to a discovery of a novel compound which can be used as an intermediate for the synthesis of (Z,E)-9,12-tetradecadienyl acetate without the above described problems and disadvantages in the prior art methods.

SUMMARY OF THE INVENTION

Thus, the novel compound provided by the present invention is a 1-halo-(Z,E)-7,10-dodecadiene represented by the general formula

(I)

in which X is an atom of chlorine or bromine.

The above defined novel compound 1-halo-(Z,E)-7,10-dodecadiene of the general formula (I) can be synthesized by a method which comprises the steps of: (a) reacting a Grignard reagent 8-halo-1-octynyl magnesium halide of the formula $XMgC \equiv C(CH_2)_6X$, in which X has the same meaning as defined above, with a substituted 2-butene compound represented by the general formula $CH_3CH = ^{(E)}CHCH_2R$, in which R is an atom or group selected from the class consisting of a chlorine atom, bromine atom, mesyloxy group and tosyloxy group, to form an ene-yne compound 1-halo-(E)-10-dodecen-7-yne of the general formula $CH_3CH = ^{(E)}CHCH_2C \equiv C(CH_2)_6X$; and (b) partially hydrogenating the ene-yne compound.

DETAILED DESCRIPTION OF THE PREFERRED EMBODIMENTS

The 1-halo-(Z,E)-7,10-dodecadiene of the general formula (I) provided by the present invention is a novel compound not described in any prior art literatures and it is useful as an intermediate for the synthesis of (Z,E)-9,12-tetradecadienyl acetate which is a sex pheromone compound of the insects belonging to the genus of Spodoptera and can be used for the purpose of population control of these noxious pests.

The 1-halo-(Z,E)-7,10-dodecadiene of the invention can be synthesized by a method comprising the steps of: (a) reacting a Grignard reagent 8-halo-1-octynyl magnesium halide of the formula $XMg \equiv C(CH_2)_6X$, in which X has the same meaning as defined above, with a substituted 2-butene compound of the general formula $CH_3CH = ^{(E)}CHCH_2R$, in which R is an atom or group selected from the class consisting of a chlorine atom, bromine atom, mesyloxy group of the formula $-OSO_2CH_3$ or tosyloxy group of the formula $-OSO_2C_6H_4CH_3$ to form an ene-yne compound and then (b) partially hydrogenating the ene-yne compound. The Grignard reagent used in the first step reaction is exemplified by 8-chloro-1-octynyl magnesium chloride, 8-bromo-1-octynyl magnesium chloride, 8-chloro-1-octynyl magnesium bromide and the like. The substituted 2-butene compound to be reacted with the Grignard reagent is exemplified by (E)-2-butenyl chloride, i.e. crotyl chloride, (E)-2-butenyl bromide, i.e. crotyl bromide, (E)-2-buten-1-ol mesylate, (E)-2-buten-1-ol tosylate and the like.

The reaction of the Grignard reagent and the substituted 2-butene compound is performed by dissolving the Grignard reagent and the substituted 2-butene compound in a suitable organic solvent such as tetrahydrofuran, diethyl ether, dioxane, butyl ether and the like or a solvent mixture thereof with toluene, benzene and the like and then the solution is admixed dropwise with the substituted 2-butene compound at a temperature of 0° to 90° C. or, preferably, 30° to 70° C. in the presence of 0.5 to 5 g of a copper (I) compound, such as copper (I) chloride, copper (I) bromide, copper (I) iodide and the like, as a catalyst per mole of the Grignard reagent. The substituted 2-butene compound is preferably (E)-2-butenyl chloride or bromide rather than (E)-2-buten-1-ol mesylate or tosylate in respect of the higher yield of the reaction product. The amount of the substituted 2-butene compound added to the solution of the Grignard reagent may be about equimolar to the Grignard reagent. The principal product of the reaction is the ene-yne compound 1-halo-(E)-10-dodecen-7-yne of the E-form with possible formation of the Z-isomer and the product of the allyl rearrangement reaction as the by-product although the yield of each of these by-products rarely exceeds 10%. Formation of these by-products causes no particular difficulties in the subsequent step because these by-product compounds can be easily separated from the principal product by distillation under reduced pressure.

The thus obtained ene-yne compound is then partially hydrogenated to give the desired 1-halo-(Z,E)-7,10-dodecadiene. The hydrogenation reaction can be performed under a hydrogen pressure of 1 to 10 kg/cm² in the pressence of a hydrogenation catalyst such as P-2 Ni catalyst and Pd-BaSO$_4$ catalyst or the same catalyst poisoned with ethylene diamine and the like in an amount of 0.001 to 0.1 mole of the metallic element per mole of the substrate compound. The reaction temperature is in the range from 0° to 70° C. It is preferable in order to avoid possible conversion of the desired reaction product into a conjugated diene compound at a high temperature and under a high hydrogen pressure that the partial hydrogenation reaction is performed at a temperature in the range from 0° to 30° C. under a hydrogen pressure of 2 to 5 kg/cm² in the presence of a P-2 Ni catalyst poisoned with ethylene diamine. When the reaction is performed in this manner, the resultant reaction mixture contains the desired 1-halo-(Z,E)-7,10-dodecadiene in a geometrical purity of at least 83%. The thus obtained 1-halo-(Z,E)-7,10-dodecadiene is a useful compound as an intermediate for the synthesis of (Z,E)-9,12-tetradecadienyl acetate which is a sex pheromone compound of the insects of the genus of Spodoptera. Namely, the 1-halo-(Z,E)-7,10-dodecadiene is first reacted with magnesium and then with ethylene oxide followed by the acetylation reaction according to the reaction scheme including the following steps.

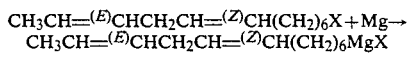

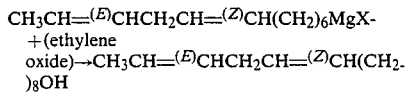

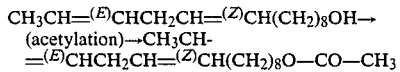

These reactions are performed, for example, by dissolving 1 mole of the 1-halo-(Z,E)-7,10-dodecadiene in 100 to 400 g of a suitable organic solvent such as tetrahydrofuran and reacting ths starting compound with magnesium in the solution to form the Grignard compound followed by the addition of ethylene oxide to the reaction mixture in an amount of about 1.5 moles per mole of the starting compound to effect the reaction at a temperature of 10° to 70° C. or, preferably, 30° to 50° C. in the presence of copper (I) chloride as a catalyst in an amount of, for example, 5 g per mole of the starting compound. The acetylation reaction is performed using acetyl chloride or acetic anhydride as the acetylating agent in the presence of various kinds of bases or using acetic acid as the acetylating agent in the presence of a catalyst. The reaction mixture obtained in this manner usually contains the desired product of (Z,E)-9,12-tetradecadienyl acetate in a geometrical purity of at least 83%.

In the following, the present invention is described in more detail by way of examples.

EXAMPLE 1

A Grignard mixture containing 3 moles of 8-chloro-1-octynyl magnesium chloride in 900 g of tetrahydrofuran was introduced into a reaction vessel and agitated for several minutes with addition of 3 g of copper (I) chloride. Thereaftere, 271.5 g (3 moles) of (E)-2-butenyl chloride were added dropwise to the mixture which was kept at a temperature not to exceed 65° C. followed by further continued agitation for 1.5 hours to complete the reaction. Thereafter, 800 g of an aqueous solution containing 5% ammonium chloride and 5% hydrogen chloride were added to the reaction mixture to effect the hydrolysis. The mixture was then subjected to phase separation and the organic phase was freed from tetrahydrofuran and then to rectification distillation to give 451 g of 1-chloro-(E)-10-dodecen-7-yne having a purity of 95%. The yield of this compound was 72% of the theoretical value.

Separately, a P-2 Ni catalyst was prepared by dissolving 3.1 g of nickel acetate in 200 g of anhydrous ethyl alcohol with addition of 0.5 g of sodium borohydride. An autoclave was charged with 123 g of the above obtained 1-chloro-(E)-10-dodecen-7-yne, 2.5 g of ethylene diamine and the above prepared P-2 Ni catalyst to effect the hydrogenation reaction under a hydrogen pressure of 2 kg/cm² at a temperature of 30° C. After completion of the reaction, 300 ml of n-hexane and 200 ml of water were added to the reaction mixture followed by phase separation to take the organic phase which was freed from n-hexane and then distilled to give 122 g of a fraction boiling at 97° to 101° C. under a pressure of 1 mmHg, which could be identified by analysis to contain 1-chloro-(Z,E)-7,10-dodecadiene in a purity of 88%. The yield of this product was 99% of the theoretical value. The analytical results leading to the identification of this product were as follows.

| (1) Infrared absorption spectrum | |
|---|---|
| 3010 cm$^{-1}$: | =CH— |
| 2960 cm$^{-1}$: | —CH$_3$ |
| 2935 cm$^{-1}$: | —CH$_2$— |
| 965 cm$^{-1}$: | —CH=CH-(trans) |
| 720 cm$^{-1}$: | —CH=CH-(cis) |
| (2) $^1$H NMR | |
| 1.32–1.42 ppm: | —CH$_2$—CH$_2$—CH$_2$— |
| 1.62 ppm: | =C—CH$_2$ |
| 1.84 ppm: | Cl—C—CH$_2$ |
| 2.04 ppm: | —C—CH$_2$—C= |
| 2.71 ppm: | =C—CH$_2$—C= |
| 3.52 ppm: | Cl—CH$_2$— |
| 5.3–5.5 ppm: | —CH=CH—C—CH=CH— |

(3) $^{13}$C NMR (unit: ppm)

$$Cl-\underset{44.97}{CH_2}-\underset{32.56}{CH_2}-\underset{26.70}{CH_2}-\underset{28.42}{CH_2}-\underset{29.37}{CH_2}-\underset{26.88}{CH_2}-\underset{130.01}{CH}=\underset{127.83}{CH}-\underset{29.49}{CH}-\underset{30.36}{CH_2}-\underset{17.81}{CH}=\underset{125.02}{CH}-\underset{}{CH_3}$$

(4) Mass spectrometric data:
m/z=200 and 202 (molecular ion peaks).

EXAMPLE 2

The synthetic procedure was substantially the same as in Example 1 excepting replacement of 271.5 g of (E)-2-butenyl chloride with 405 g of (E)-2-butenyl bromide to give 469 g of a product after hydrolysis which could be identified by analysis to be 1-chloro-(E)-10-dodecen-7-yne in a purity of 95%. The yield was 75% of the theoretical value. Partial hydrogenation of this ene-yne compound in the same manner as in Example 1 gave 447 g of 1-chloro-(Z,E)-7,10-dodecadiene in a purity of 89%. The yield was 96% of the theoretical value.

EXAMPLE 3

The synthetic procedure was about the same as in Example 1 excepting replacement of 271.5 g of (E)-2-butenyl chloride with 450 g (3 moles) of (E)-2-buten-1-ol mesylate which were added dropwise to the reaction mixture kept at 30° C. or below followed by further continued agitation of the reaction mixture at 30° C. for 1.5 hours to effect hydrolysis so that 216 g of 1-chloro-(E)-10-dodecen-7-yne were obtained in a purity of 94%. The yield was 35% of the theoretical value. Partial hydrogenation of this ene-yne compound in the same manner as in Example 1 gave 203 g of 1-chloro-(Z,E)-7,10-dodecadiene in a purity of 88%. The yield was 88% of the theoretical value.

EXAMPLE 4

The synthetic procedure was substantially the same as in Example 3 excepting replacement of 450 g of (E)-2-buten-1-ol mesylate with 678 g of (E)-2-buten-1-ol tosylate which was reacted with the starting Grignard reagent followed by hydrolysis to give 262 g of 1-chloro-(E)-10-dodecen-7-yne in a purity of 93%. The yield was 41% of the theoretical value. Partial hydrogenation of this ene-yne compound in the same manner as in Example 1 gave 230 g of 1-chloro-(Z,E)-7,10-dodecadiene in a purity of 87%. The yield was 82% of the theoretical value.

EXAMPLE 5

The experimental procedure was substantially the same as in Example 1 except that the starting Grignard mixture contained 3 moles of 8-bromo-1-octynyl magnesium chloride in tetrahydrofuran in place of 8-chloro-1-octynyl magnesium chloride to give 529 g of 1-bromo-(E)-10-dodecen-7-yne in a purity of 95%. The yield was 69% of the theoretical value. Partial hydrogenation of 150.5 g of this ene-yne compound in the same manner as in Example 1 gave 145 g of a product boiling at 106° to 110° C. under a pressure of 1 mmHg, which could be identified by analysis to be 1-bromo-(Z,E)-7,10-dodecadiene. The analytical data leading to the identification of this product compound were as follows.

| (1) Infrared absorption spectrum | |
|---|---|
| 3010 cm$^{-1}$: | =CH— |
| 2960 cm$^{-1}$: | —CH$_3$ |
| 2935 cm$^{-1}$: | —CH$_2$ |
| 965 cm$^{-1}$: | —CH=CH-(trans) |
| 720 cm$^{-1}$: | —CH=CH-(cis) |
| (2) $^1$H NMR | |
| 1.32–1.42 ppm: | —CH$_2$—CH$_2$—CH$_2$— |
| 1.65 ppm: | =C—CH$_3$ |
| 1.85 ppm: | Br—C—CH$_2$ |
| 2.05 ppm: | —C—CH$_2$—C= |
| 2.73 ppm: | =C—CH$_2$—C= |
| 3.41 ppm: | Br—CH$_2$— |
| 5.35–5.45 ppm: | —CH=CH—C—CH=CH— |

(3) $^{13}$C NMR (unit: ppm)

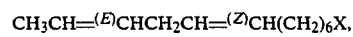

(4) Mass spectrometric data:
m/z=244 and 246 (molecular ion peaks).

EXAMPLE 6

(Z,E)-9,12-Tetradecadienyl acetate was synthesized in the following manner. Thus, 17 g of magnesium and 250 g of tetrahydrofuran were introduced into a reaction vessel and 140 g of 1-chloro-(Z,E)-7,10-dodecadiene were added dropwise thereto followed by heating of the mixture at 75° C. for 2 hours to give (Z,E)-7,10-dodecadienyl magnesium chloride.

Thereafter, the thus obtained Grignard mixture was cooled to 20° C. and agitated for several minutes with addition of 3.2 g of copper (I) chloride followed by dropwise addition of 43 g of ethylene oxide to the mixture kept at a temperature of 35° to 45° C. After completion of the dropwise addition of ethylene oxide, the reaction mixture was further agitated at 45° C. for additional 1 hour and then 300 g of an aqueous solution containing 5% of ammonium chloride and 5% of hydrogen chloride were added thereto. The organic phase taken by phase separation and freed from tetrahydrofuran by distillation under reduced pressure was admixed with 300 g of n-hexane, 100 g of triethyl amine and 100 g of acetic anhydride to effect the acetylation reaction for 2 hours under reflux at 70° C. After completion of the reaction, 400 ml of water were added to the reaction mixture from which the organic phase was taken by phase separation and freed from n-hexane followed by rectification distillation to give 150 g of (Z,E)-9,12-tetradecadienyl acetate in a purity of 84%. The yield was 71% of the theoretical value.

What is claimed is:

1. 1-Halo-(Z,E)-7,10-dodecadiene represented by the general formula

CH$_3$CH=$^{(E)}$CHCH$_2$CH=$^{(Z)}$CH(CH$_2$)$_6$X, in which X is a chlorine atom or a bromine atom.

2. The 1-halo-(Z,E)-7,10-dodecadiene as claimed in claim 1 wherein X is a chlorine atom.

3. The 1-halo-(Z,E)-7,10-dodecadiene as claimed in claim 1 wherein X is a bromine atom.

* * * * *